United States Patent [19]
Grasso, deceased

[11] Patent Number: 5,211,660
[45] Date of Patent: May 18, 1993

[54] METHOD FOR PERFORMING EPIKERATOPHAKIA BY ELECTROFUSION

[75] Inventor: Robert J. Grasso, deceased, late of Tampa, Fla., by Carol Grasso, executor

[73] Assignee: University of South Florida, Tampa, Fla.

[21] Appl. No.: 574,172

[22] Filed: Aug. 28, 1990

Related U.S. Application Data

[63] Continuation-in-part of Ser. No. 189,206, May 2, 1988, abandoned, and a continuation-in-part of Ser. No. 297,218, Jan. 17, 1989, Pat. No. 4,955,378.

[51] Int. Cl.⁵ ............................ A61F 2/14; A61N 1/32; A61N 1/00
[52] U.S. Cl. ......................................... 623/5; 128/421; 128/793; 128/898; 606/107

[58] Field of Search ............... 623/4, 5; 128/421, 788, 128/793, 897-899; 604/20; 606/107

[56] References Cited

U.S. PATENT DOCUMENTS
4,662,881  5/1987  Nordan ..................................... 623/5
4,676,790  6/1987  Kern ................................. 128/898 X

FOREIGN PATENT DOCUMENTS
1503802  8/1989  U.S.S.R. ............................. 128/898

Primary Examiner—Ronald Frinks
Attorney, Agent, or Firm—Joseph C. Mason, Jr.; Ronald E. Smith

[57] ABSTRACT

An improved epikeratophakia utilizing electrofusion to graft donor corneal tissue to patient's cornea.

26 Claims, 2 Drawing Sheets

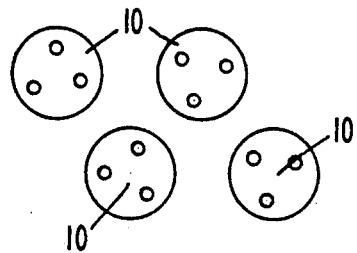
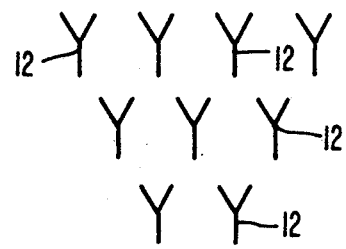
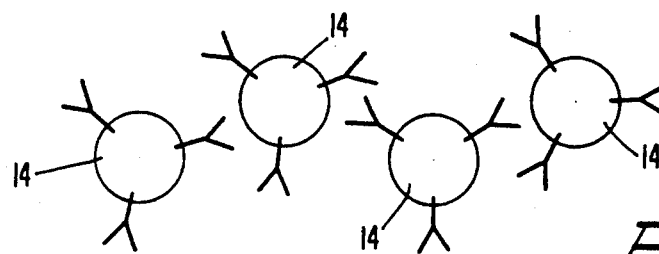
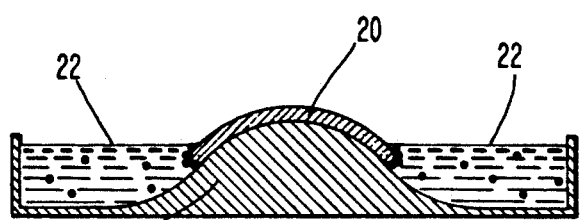
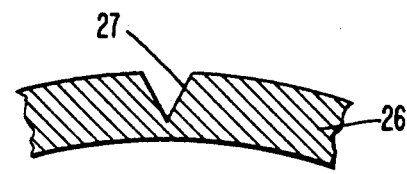
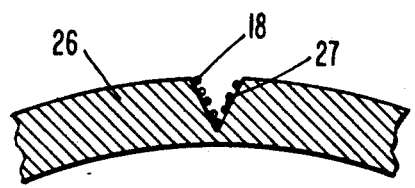
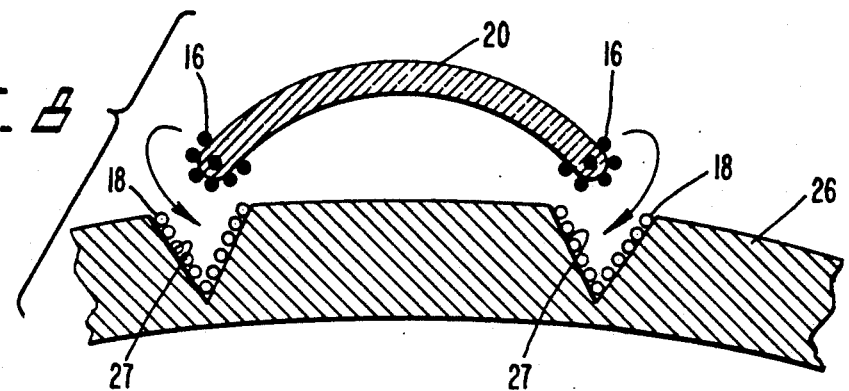

METHOD FOR PERFORMING EPIKERATOPHAKIA BY ELECTROFUSION

CROSS REFERENCE TO RELATED APPLICATIONS

The present disclosure is a continuation in-part of co-pending application filed May 2, 1988, by the present inventor and entitled "Method for Electrofusing Biological Particles to Tissues," Ser. No. 07/189,206, now abandoned and co-pending application filed Jan. 17, 1989, by the present inventor and entitled "Apparatus and Methods for Performing Electrofusion at Specific Anatomical Sites," Ser. No. 07/297,218, now U.S. Pat. No. 4,955,378; both of which are incorporated herein by reference thereto.

BACKGROUND OF THE INVENTION

This invention relates to the treatment of the mammalian eye; human and animal. It also relates to optical onlay lamellar keratoplasty that changes the topography and topolomy of the anterior corneal surface, which results in the alteration of the refracting power of the cornea. It specifically relates to improvements in the epikeratophakia process.

Epikeratophakia are surgically performed on patients unable to have their vision problems corrected by penetrating keratoplasty, corrective lenses, or for various medical reasons. The ocular conditions that can be corrected by epikeratophakia consist of keratophakia, keratomileusis, aphakia, keratoconus and myopia. U.S. Pat. No. 4,662,881 is representative of prior art epikeratophakia.

More specifically, the prior art epikeratophakia process or surgery is generally performed in the following steps: (1) the appropriate corneal topography to correct the manifested problem is identified by reference to specific location; (2) lyophilized donor tissues are obtained and made readily available; such donor tissue consists of stroma lacking endothelium and epithelium appropriately shaped by a specific computer program; (3) perform annular keratectomy by trephination some distance away from the axis of the optical corneal center; such procedure is to remove optical field corneal epithelium, but not stromal tissue, from the patient's eye; (4) rehydrate the computerized shaped cornea; (5) place rehydrated cornea into correct position within the keratectomy site; (6) suture such donor tissue to patient's cornea at the keratectomy site; (7) treat the surgical site with antibiotics and anti-inflammatory agents. The aforesaid prior art procedure excites the process whereby keratocytes migrate from the patient's stroma into the donor tissue with reepithelialization occurring over the transplanted tissue within days.

There are major disadvantages to the prior art epikeratophakia. The major disadvantage is suturing the donor corneal material to the patient's cornea. As others have expressed, this is a difficult operation which requires great skill and precision. In addition, the appropriate corneal topography to correct the vision problem is distorted by the suturing procedures. In short, suturing results in diminished visual benefits to the patient and represents a risk to the patient.

It is also well known that extensive inflammation usually occurs after suturing requiring careful postoperative monitoring and treatment for the inflammation.

Suturing of the donor corneal material to the patient's cornea is very time consuming, e.g., at least one hour per eye; therefore, the patient is under the surgical procedure for a relatively long time and invariably ocular infections result because of the length of time required for suturing.

Severe or uncontrolled blepharitis, dry eyes or lagophthalmos are contraindicated for the prior art procedures currently employed for epikeratophakia surgery.

SUMMARY OF THE INVENTION

The invention provides an improved process for performing epikeratophakia surgery. It specifically provides an improved process for performing epikeratophakia surgery by in vivo electrofusion biotechnology.

It is an object of this invention to perform epikeratophakia surgery without the need for suturing donor tissues to the patient's cornea thereby avoiding distortion of the corneal surface.

Another object of the invention is to more strongly fix the donor corneal tissue to the patient's cornea.

A further object of the invention is to provide a procedure for epikeratophakia surgery that is simple and amenable to standardization.

A still further object of the invention is to provide a epikeratophakia procedure which avoids or drastically reduces ocular infection and ocular inflammation.

These and other objects are accomplished by a electrofusion process as a substitute for suturing employing electrodes having the appropriately prescribed topology that will mirror the prescribed topology of the cornea as ordered by the ophthalmologist. The inventive electrofusion technique, preferably, utilizes the patient's own monocytes with the resulting benefit of diminished problems of immunological rejection.

BRIEF DESCRIPTION OF THE DRAWINGS

For a fuller understanding of the nature and objects of the invention, reference should be made to the following detailed description, taken in connection with the accompanying drawings, in which:

FIG. 1 is a diagrammatic view showing a patient's monocytes with surface Fc receptors;

FIG. 2 is a diagrammatic view showing anti-human collagen antibodies;

FIG. 3 is a diagrammatic view showing mixed cells and antibodies, i.e., FIG. 3 shows the product of mixing the cells of FIG. 1 and the antibodies of FIG. 2;

FIG. 4 is a diagrammatic view of sensitized monocytes;

FIG. 5 is a sectional, side elevational view of a raised globular plate for binding preselected sensitized monocytes to the periphery of donor tissue;

FIG. 6 is a sectional, side elevational view of a patient's cornea showing the preparation of an annular keratectomy thereon;

FIG. 7 is a sectional, side elevational view of the patient's cornea showing the binding of sensitized monocytes to the internal annular keratectomy site;

FIG. 8 is a sectional, side elevational, exploded view showing how the periphery of the donor graft is inserted into the annular keratectomy site;

BEST MODE OR PREFERRED EMBODIMENT OF THE INVENTION

Figure 9:
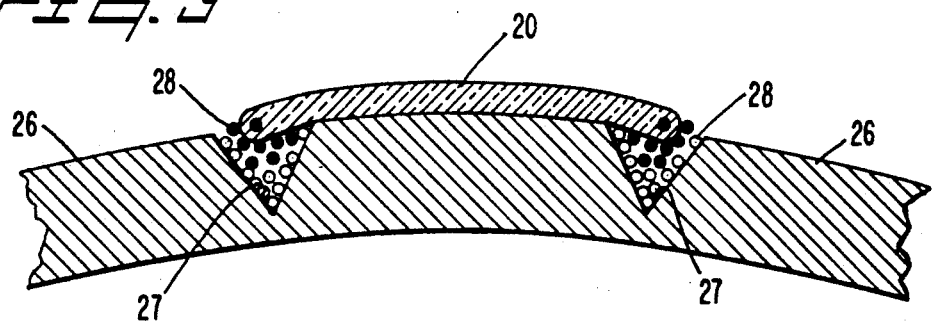
FIG. 9 is a side elevational, sectional view of the patient's cornea showing the attachment of the donor tissue to the patient's cornea as a result of the sensitized monocytes being bound to the donor tissue and the keratectomy site.

Referring to FIG. 1, a patient's mononuclear phagocytic leukocytes or monocytes 10 with surface Fc receptors are obtained from a blood source, preferably, the patient's own blood source. In its preferred embodiment, the Fc receptor site is suitable for one of the two segments of the IgG molecule; although, in practice, the receptor site may be suitable for any one of the five classes of heavy chain immunoglobulins, such as IgA, IgD, IgE, IgG, and IgM, with similar results.

The IgG collagen antibody 12 (FIG. 2) is admixed (FIG. 3) with the patient's monocytes (FIG. 1) to form sensitized monocytes 16 (FIG. 4).

Donor corneal tissue 20 (FIG. 5) is obtained from a commercial source and the hyperopic or myopic correction is applied, typically, by computer programmed carving (not shown). Tissue 20 is rehydrated and placed or layered on a raised globulan plate 24 such that a reservoir 22 is available along the periphery of donor tissue 20.

A portion 16 of the sensitized monocytes 14 is placed in the reservoir 22 and bound to the peripheral area of the donor tissue 20; i.e., the IgG-coated monocytes 16 bind only to the periphery of the donor tissue 20 graft. Thus, the monocytes become available for electrofusion after the antibodies bind to the collagen in the peripheral regions of the donor stroma.

The patient's cornea 26 (FIG. 6) is prepared to receive the donor tissue 20 graft by creation of annular keratectomy site 27 by trephination on patient's cornea 26.

A further portion 18 of sensitized monocytes 14 is transferred into the crevice of the annular keratectomy site as shown in FIG. 7. Thus, the monocytes 18 becomes available for electrofusion after the antibodies bind to the collagen in the patient's stroma.

The donor tissue 20 graft having the bound sensitized monocytes 16 along its periphery is inserted into the crevice 27 of the annular keratectomy site of patient's cornea 26 having the bound sensitized monocytes 18 along such crevice (see FIG. 8), so that monocytes 16 and monocytes 18 are in contact, as shown at 28 of FIG. 9. Preferably, all ocular tissues are rinsed extensively with a sterile non-electrolytic buffer. This rinsing step will decrease the probability of the induced electrical field traveling across the ocular surface between the electrodes, more fully described hereinbelow.

Figure 10:
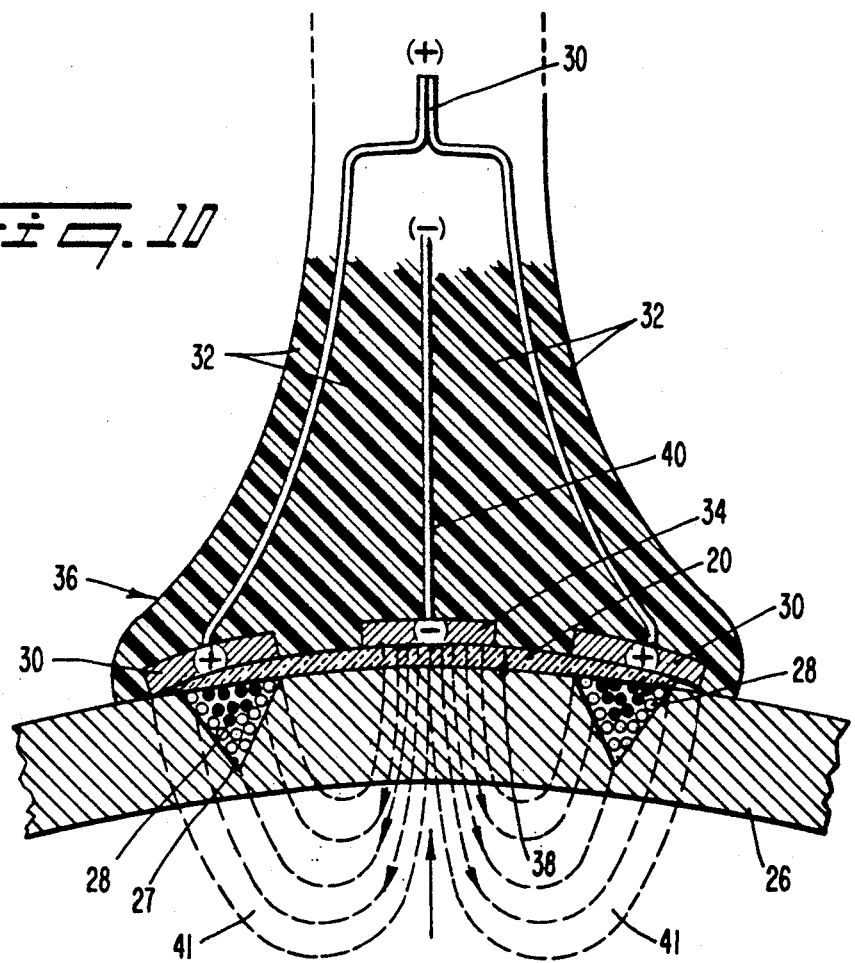
FIG. 10 is a sectional, side elevational view of a single unit customized electrode (anode over the keratectomy site, cathode over optical axis)

Referring now to FIG. 10, a single unit customized electrofusion instrument 36, as generally described in copending patent application Ser. No. 07/297,218, now U.S. Pat. No. 4,955,378 is positioned on the ocular surface. The electrofusion instrument 36 has anodes 30 which are formed as a curved corneal disc 38 in the "mirror" image of the dimensions of donor tissue 20. The anodial zone is over the annular keratectomy site 27. The cathode 34 is positioned over the optic axis 40.

A direct current electrical charge from a source (not shown) creates an induced electrical field shown generally as 41. A slight mechanical force, such as by the surgeon providing slightly downward pressure on the instrument, is applied to maintain the monocytes, collectively shown as 28, within crevice 27. The donor tissue 20 graft is electrofused to the patient's cornea 26 within minutes, e.g., one to ten minutes. The grafting occurs by the fusion of the monocytes 16 bound to the periphery of donor tissue 20 and the monocytes 18 bound to the patient's stroma within the annular kerectomy site crevice 27.

Figure 11:
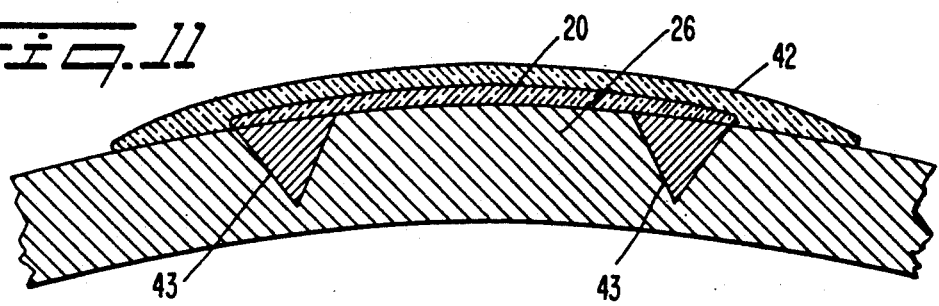
FIG. 11 is a sectional, side elevational view showing a contact lens place over the donor tissue and indicating the electrofused areas.

After removal of the electrode unit from the ocular surface, preferably a contact lens 42 is placed over the corneal surface to prevent movement of the electrofused tissue 20, as shown in FIG. 11. Keratocytes from the patient migrate into the donor tissue; reepithelialization occurs over a relatively short period of time, e.g., a few days, after which the contact lens is removed.

In one broad embodiment, the methods of the present invention generally comprise the following steps:

(1) Obtain computer shaped donor corneal tissue and rehydrate such donor tissue.

(2) Prepare electrode device shaped and dimensioned to the opposite topology, e.g., concave, of the corrected corneal surface, e.g., convex. As described in co-pending application Ser. No. 07/297,218, this electrode device consists of two (2) electrodes separated by an insulator and typically will be constructed as a single unit.

(3) Prepare purified monocytes, preferably, from patient's own blood.

(4) Bind such monocytes to anticollagen antibodies, e.g., IgG, via respective Fc regions.

(5) Layer rehydrated donor tissue on raised globular plates designed to bind the IgG-coated monocytes only to the periphery of the graft. This technique delivers the monocytes to the electrofusion site after the antibodies bind to the collagen in the peripheral regions of the donor stroma.

(6) Prepare annular keratectomy site by trephination on patient's cornea.

(7) Introduce IgG-coated monocytes into the crevice of the annular keratectomy site. At this stage of the procedure, monocytes become available for electrofusion after the antibodies bind to the collagen in the patient's stroma.

(8) Position the donor tissue graft into keratectomy site crevice.

(9) Rinse all ocular tissues extensively with a sterile non-electrolytic buffer.

(10) Introduce the electrode device of Step (2) in contact with the ocular surface such that one electrode, i.e., the anode, is in contact with the annular keratectomy site and the other electrode, i.e., the cathode, is positioned over the axis of the optical field.

(11) Deliver the optimal electromechanical parameters to this globe such that the donor tissuegraft is electrofused to the patient's corneal tissue within a relatively short time, e.g., 1 to 10 minutes. This Step (11) results in the fusion of monocytes which are bound strongly to the donor tissuegraft periphery and the monocytes which are strongly bound to the patient's stroma within the keratectomy crevice.

(12) Optionally, but preferably, a contact lens is placed over the corneal surface to prevent movement of the electrofused tissue until keratocytes from the patient migrate into the donor tissue at which point reepithelialization occurs. The contact lens may now be removed.

Thus, the present invention provides an improved method for correcting ophthalmic defects using epikeratophakia in which shaped and lyophilized donor corneal tissue is rehydrated and electrofused to the patient's own cornea.

Another embodiment of the present invention is epikeratophakia comprising the steps of:

(a) contacting donor cornea tissue having preselected topology of convex dimensions with patient's own cornea surface, and (b) subjecting the donor cornea tissue and patient's cornea to an electric field under conditions sufficient to fuse the donor tissue to patient's cornea.

In order to assure electrofusion integrity, the donor cornea tissue is contacted with the patient's cornea using mechanical force. Such force can be created by any means but typically will result from slight pressure on the instrument by the surgeon. In a more specific embodiment, such mechanical force is applied by a device having concave dimensions congruent to or a "mirror" image of the preselected convex dimensions of the donor tissue. In each embodiment, the electrical field comprises a direct current electrical field. Basically, the direct current electrical field is created by applying a pulse of direct current to an electrode juxtaposed with the donor cornea tissue and patient's own cornea. Preferably, the direct current field is created by applying multiple pulses of direct current to an electrode juxtaposed with the selected donor cornea tissue and patient's cornea.

A still further embodiment of the present invention is epikeratophakia comprising the steps of:

(a) obtaining a donor corneal tissue suitable for grafting to patient's cornea to correct a diagnosed hyperoxic or myopic defect;

(b) forming a crevice in patient's cornea by cutting a peripheral groove therein;

(c) obtaining monocytes from a blood source;

(d) introducing a first portion of the monocytes into the crevice;

(e) introducing a second portion of the monocytes in binding relationship to the periphery of the donor corneal tissue;

(f) positioning the donor cornea tissue in congruent relationship with patient's cornea such that the first portion of monocytes is in direct contact with the second portion of monocytes; and (g) subjecting the positioned donor corneal tissue and patient's cornea to an electric field under conditions sufficient to graft the donor corneal tissue to patient's cornea.

In order to assure electrofusion integrity, the contact between the first portion of monocytes and the second portion of monocytes is provided by mechanical force as aforesaid.

A still further specific embodiment of the present invention is a method for corneal grafting which comprises the steps of:

(a) obtaining a hydrated shaped donor corneal tissue having a preselected dimensional shape;

(b) preparing annular keratectomy site by trephination of a crevice on patient's cornea;

(c) obtaining mononuclear phagocytic leukocytes from a blood source;

(d) sensitizing the mononuclear phagocytic leukocyte by admixing with a suitable anticollagen antibody at the Fc regions;

(e) depositing the hydrated shaped donor corneal tissue on a hemispherical shaped plate to form a peripheral reservoir about the donor tissue;

(f) introducing the first portion of sensitized mononuclear phagocytic leukocytes into the peripheral reservoir under conditions sufficient to bind such mononuclear phagocytic leukocytes to the donor tissue; thereby forming a graft donor tissue;

(g) introducing a second portion of the sensitized mononuclear phagocytic leukocytes into the annular keratectomy site on the patient's cornea;

(h) positioning the graft donor tissue into the keratectomy site crevice in patient's cornea; and, (i) subjecting the graft donor tissue and the patient's cornea to an electrical field while maintaining the graft donor tissue positioned into the keratectomy site crevice in patient's cornea, under conditions sufficient to graft the donor tissue to patient's cornea by fusion.

Preferably, the blood source is the patient's own blood. Also, the antibody comprises immunoglobulin selected from the classes consisting of IgA, IgD, IgE, IgG, and IgM; preferably the IgG class.

An additional embodiment includes the further steps of removing the electrofusion device or instrument and placing a blank contact lens over the graft as protection thereto.

Other refinements or embodiments of the invention include the creation of the direct current electrical field by applying a pulse of direct current through one electrode in contact with the annular keratectomy site in the patient's cornea and a second electrode positioned over the optic axis in contact with the graft donor tissue.

Having described a number of embodiments of the methods of this invention, it is apparent to those skilled in the art in contact with the annular keratectomy site in the patient's cornea and a second electrode positioned over the optic axis in contact with the graft donor tissue.

Having described a number of embodiments of the methods of this invention, it is apparent to those skilled in the art that various changes and modifications may be made without departing from the spirit and scope of the invention as defined by the claims appended hereto.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. Epikeratophakia comprising the steps of:
   (a) contacting donor cornea tissue having preselected topology of convex dimensions with a patient's own cornea, using mechanical force applied by a device having concave dimensions congruent to the preselected convex dimensions of said donor tissue; and
   (b) subjecting the donor cornea tissue and the patient's cornea to an electrical field under conditions sufficient to fuse the donor tissue to the patient's cornea.

2. Epikeratophakia according to claim 1 wherein the device comprises an electrofusion instrument.

3. Epikeratophakia according to claim 1 wherein the electrical field comprises a direct current electric field.

4. Epikeratophakia according to claim 3 wherein the direct current electrical field is created by applying a pulse of direct current to an electrode juxtaposed with the donor cornea tissue and patient's own cornea.

5. Epikeratophakia according to claim 2 wherein the electric field comprises a direct current electric field.

6. Epikeratophakia according to claim 5 wherein the direct current field is created by applying a pulse of direct current to an electrode juxtaposed with the donor cornea tissue and patient's own cornea.

7. Epikeratophakia comprising the steps of:
(a) obtaining a donor corneal tissue suitable for grafting to patient's cornea to correct a diagnosed hyperopic or myopic defect;
(b) forming a crevice in patient's cornea by cutting a peripheral groove therein;
(c) obtaining monocytes from a blood source;
(d) introducing a first portion of the monocytes into the crevice;
(e) introducing a second portion of the monocytes in binding relationship to the periphery of the donor corneal tissue;
(f) positioning the donor corneal tissue in congruent relationship with patient's cornea such that the first portion of monocytes is in direct contact with the second portion of monocytes; and
(g) subjecting the positioned donor corneal tissue and patient's cornea to an electric field under conditions sufficient to graft the donor corneal tissue to patient's cornea.

8. Epikeratophakia according to claim 7 wherein the contact between the first portion of monocytes and the second portion of monocytes is provided by mechanical force.

9. Epikeratophakia according to claim 8 wherein the mechanical force is applied by a device having concave dimensions congruent to the preselected convex dimensions of the donor corneal tissue.

10. Epikeratophakia according to claim 9 wherein the device comprises an electrofusion instrument.

11. Epikeratophakia according to claim 7 wherein the electrical field comprises a direct current electrical field.

12. Epikeratophakia according to claim 11 wherein the direct current electrical field is created by applying a pulse of direct current to an electrode juxtaposed with the donor corneal tissue and patient's cornea.

13. Epikeratophakia according to claim 10 wherein the electrical field comprises direct current electrical field.

14. Epikeratophakia according to claim 13 wherein the direct current electrical field is created by applying a pulse of direct current to an electrode juxtaposed with the donor corneal tissue and patient's cornea.

15. Method for corneal grafting which comprises the steps of:
(a) obtaining a hydrated shaped donor corneal tissue having a preselected dimensional shape;
(b) preparing annular keratectomy site by trephination of a crevice on patient's cornea;
(c) obtaining mononuclear phagocytic leukocytes from a blood source;
(d) sensitizing the mononuclear phagocytic leukocytes by admixing with a suitable anticollagen antibody at the Fc regions;
(e) depositing the hydrated shaped donor corneal tissue on a hemispherical shaped plate to form a peripheral reservoir about the donor tissue;
(f) introducing a first portion of the sensitized mononuclear phagocytic leukocytes into peripheral reservoir under conditions sufficient to bind such mononuclear phagocytic leukocytes to the donor tissue; thereby forming a graft donor tissue;
(g) introducing a second portion of sensitized mononuclear phagocytic leukocytes into annular keratectomy site on the patient's cornea;
(h) positioning the graft donor tissue into the keratectomy site crevice in patient's cornea; and
(i) subjecting the graft donor tissue and the patient's cornea to an electrical field while maintaining the graft donor tissue positioned into the keratectomy site crevice in patient's cornea, under conditions sufficient to graft the donor tissue to patient's cornea by fusion.

16. Method according to claim 15 the blood source comprises the patient's own blood.

17. Method according to claim 15 wherein the anticollagen antibody comprises immunoglobulin from the class consisting of IgA, IgD, IgE, IgG, and IgM.

18. Method according to claim 17 wherein the immunoglobulin comprises IgG.

19. Method according to claim 15 wherein electrical field comprises a direct current electric field.

20. Method according to claim 19 where the direct current electrical field is created by applying a pulse of direct current to an electrode juxtaposed with the graft donor tissue and the patient's cornea.

21. Method according to claim 19 wherein maintaining the graft donor tissue positioned into the keratectomy site crevice in patient's cornea is by the use of mechanical force.

22. Method according to claim 21 wherein the mechanical force is applied by a device having dimensions congruent to the preselected dimensions of the hydrated shaped donor corneal tissue.

23. Method according to claim 22 wherein the device comprises an electrofusion instrument.

24. Method according to claim 23 comprising the additional steps of:
(j) removing the electrofusion device, and,
(k) placing a blank contact lens over the graft as protection thereto.

25. Method according to claim 20 wherein the direct current electrical field is created by applying a pulse of direct current through one electrode in contact with the annular keratectomy site in the patient's cornea and a second electrode positioned over the optic axis in contact with the graft donor tissue.

26. An improved epikeratophakia process, comprising the steps of:
contacting a living patient's cornea with donor cornea tissue having a preselected topology of convex dimensions; and
subjecting the donor cornea tissue and the patient's cornea to a direct current electrical field under conditions sufficient to fuse the donor tissue to the patient's cornea.

* * * * *